Figure 1:
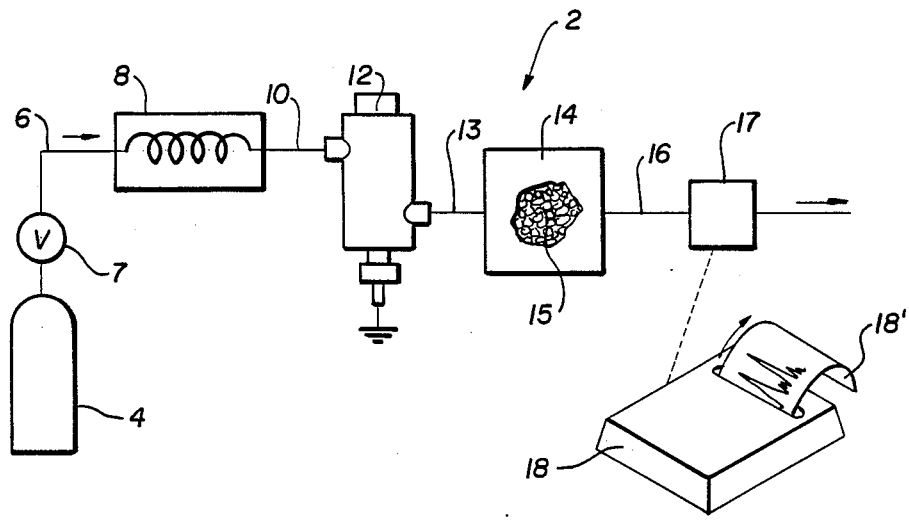

United States Patent [19]

Succi

[11] Patent Number: 4,889,814
[45] Date of Patent: Dec. 26, 1989

[54] METHOD AND APPARATUS FOR DETECTION OF TRACE IMPURITIES IN AN IMPURE INERT GAS

[75] Inventor: Marco Succi, Milan, Italy

[73] Assignee: SAES Getters SpA, Milan, Italy

[21] Appl. No.: 184,989

[22] Filed: Apr. 22, 1988

[30] Foreign Application Priority Data

May 7, 1987 [IT] Italy ................................ 20422 A/87

[51] Int. Cl.[4] .......................................... G01N 21/71
[52] U.S. Cl. .................................... 436/133; 436/141; 436/153; 422/83
[58] Field of Search .................... 422/83, 98; 436/133, 436/141, 52, 153, 171

[56] References Cited

U.S. PATENT DOCUMENTS

| | | |
|---|---|---|
| 3,266,869 | 8/1966 | Dengler . |
| 3,420,636 | 1/1969 | Robbins . |
| 3,549,327 | 12/1970 | Fergusson . |
| 3,754,867 | 8/1973 | Guenther . |
| 3,790,348 | 2/1974 | Bossart et al. ................. 422/54 |
| 3,871,827 | 3/1975 | Seiler . |
| 4,058,368 | 11/1977 | Svensson . |
| 4,063,895 | 12/1977 | Neti . |
| 4,411,867 | 10/1983 | Ostrander ...................... 422/91 |
| 4,525,328 | 6/1985 | Bredeweg . |
| 4,541,269 | 9/1985 | Thomas . |

OTHER PUBLICATIONS

Trace Analytical-RGD2-Reduction Gas Detector Bulletin #D1002 with 1-1-86 Price List-12 pages.
Trace Analytical Operating Manual-cover, pp. 4-1 and 6-2-3 pages total.
McNair et al, "Basic Gas Chromatography", pp. 108 through 110+2 cover sheets-5 pages.

Primary Examiner—Barry S. Richman
Assistant Examiner—Lyle Alfandary Alexander
Attorney, Agent, or Firm—David R. Murphy

[57] ABSTRACT

A method is described for the quantitative measurement of traces of gas, particularly $CO_2$ and $CH_4$ which constitute impurities in impure inert gases such as rare gases and nitrogen, by means of the use of a known analyzer for reducing gases which uses a bed of mecuric oxide and makes the measurement by an optical method of the mercury vapors produced which are proportional in to the concentration of the impurities to be detected. The method of the present invention subjects the impure inert gas to an electric discharge which may be at a high voltage, capable of ionizing the impurities before the impure inert gas is made to pass through the bed of mecuric oxide. The device according to the invention comprises, between a gas-chromatographic separation column and the analyzer, an electrode within a passage through which flows the gas to be analyzed and in which there is an ionizing discharge.

8 Claims, 2 Drawing Sheets

METHOD AND APPARATUS FOR DETECTION OF TRACE IMPURITIES IN AN IMPURE INERT GAS

Various methods and apparatus are known in the art for the measurement, even in low concentrations, of reducing gases, in particular CO and $H_2$ in various gases and above all in air. See for example U.S. Pat. Nos. 3,420,626; 3,871,827; and 3,790,348 (the U.S. Pat. No. '348). More recently U.S. Pat. No. 4,411,867 (the U.S. Pat. No. '867) issued based on the principle of using a bed of mercuric oxide as taught in U.S. Pat. No. 3,420,636. The U.S. Pat. No. '867 describes a very precise apparatus for the measurement of traces of CO and $H_2$ down to levels of one part per million or even one part per billion (ppb) (1 ppb = 1 in $10^9$). The measuring apparatus comprises a chromatographic column and an optical sensor for the detection of mercury vapour which is released by the reducing action of the traces of CO and $H_2$ on the bed of mercuric oxide.

Furthermore, it is known that in $N_2$ or the rare gas which is required to have the highest possible purity there are present, not only the reducing gases which are detectable by the U.S. Pat. No. '867 but there are also present other non-reducing gases, and especially $CO_2$ and $CH_4$. It is true that the U.S. Pat. No. '348 is also capable of measuring methane and total hydrocarbons present in a gas, and in particular in air, but the disclosed method, which is based on a hydrogen flame detector, does not give precise results at concentrations as low as can be obtained by the method of the U.S. Pat. No. '867. Unfortunately, the U.S. No. Pat. '867 can only detect the presence of reducing gases.

It is therefore an object of the present invention to provide a trace gas analyzer of a gas to be analyzed, such as taught in the U.S. Pat. No. '867 which is capable of analyzing traces of non-reducing gases such as $CO_2$ and $CH_4$.

A further object of the present invention is to provide a method of treatment of an impure inert gas containing impurities of reducing gases and/or non-reducing gases, for the determination of the concentration of such impurities.

This is accomplished by means of a method which comprises the known stages of causing the impure inert gas to be analyzed to pass through a gas-chromatographic separation column and across a bed of mercuric oxide for the optical detection of the quantity of mercury vapour produced by said bed, characterized by the fact of comprising, between the chromatographic separation column and the bed there is a step in which the impure inert gas is subjected to an ionizing discharge, which can be at a high voltage.

The apparatus of the present invention comprises a gas-chromatographic separation column, a reducing gas analyzer based on the use of a mercuric oxide bed, followed by a mercury vapour detector, and is characterized by the fact of comprising an ionizer in series between said separation column and said analyzer.

In one particularly preferred embodiment of said apparatus the ionizer comprises a cylindrical chamber within which there is mounted a coaxial electrode capable of generating a symmetrical discharge to the walls of said chamber.

Figure 2:
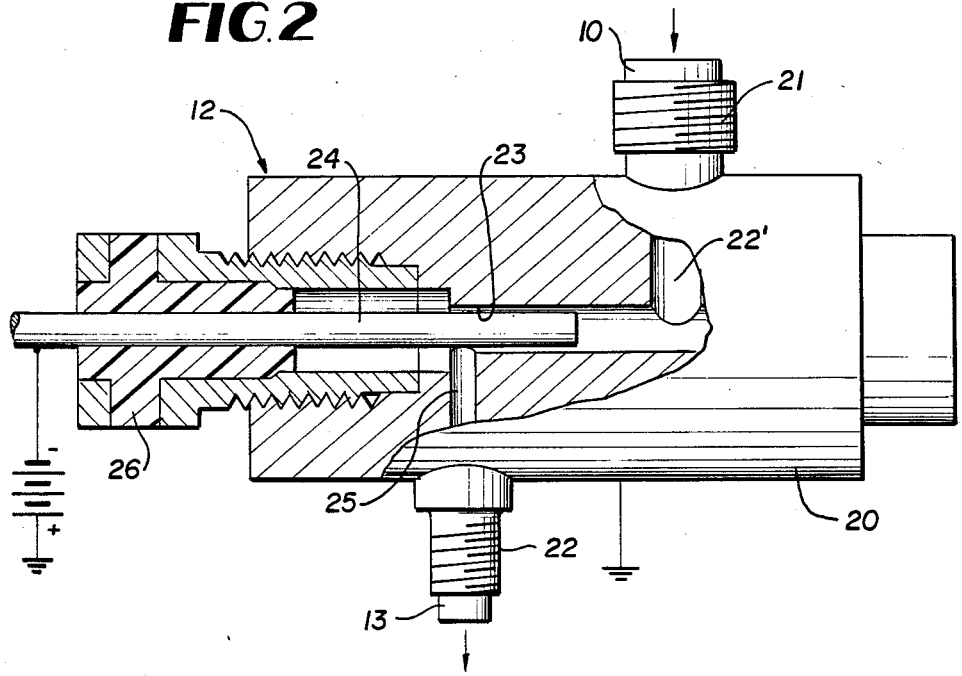
Figure 3:
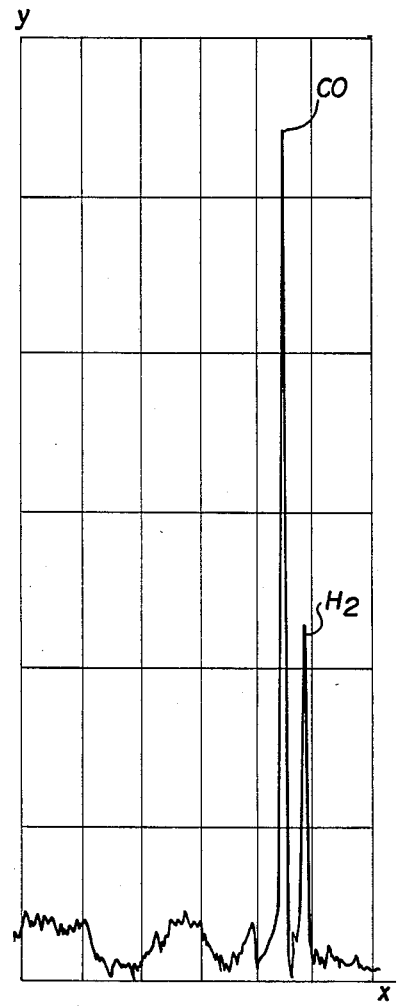

The above and other objects, characteristics, and advantages of the method and apparatus of the present invention will become evident to those skilled in the art from the following detailed description of a preferred, non-limiting embodiment, and by reference to the attached drawings in which:

FIG. 1 shows a block diagram of the complete apparatus suitable for practicing the method of the present invention; and FIG. 2 shows a cross-section of a preferred embodiment of the ionizer useful in producing an ionizing discharge in the impure inert gas to be analyzed and which allows a determination of the presence of certain trace impurities; and FIG. 3 is a graph obtained showing the peaks of CO and $H_2$ detected in an impure inert gas containing traces also of nonreducing gases. This graph was obtained using an analyzing device of the U.S. Pat. No. '867 which is to say an apparatus similar to that of in FIG. 1 but having no ionizer.

Figure 4:
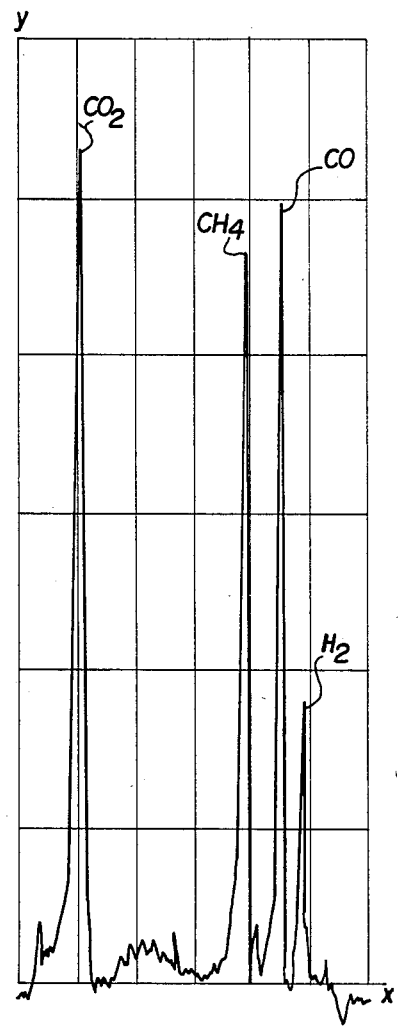

FIG. 4 shows a graph of the peaks detected from the same gas as used for FIG. 3 when analyzed according to the method of the present invention shown in FIG. 1.

Referring now to FIG. 1, there is shown an apparatus 2 suitable for practicing the process of the present invention. The apparatus 2 comprises a container 4 holding an impure inert gas. The container 4 is connected to conduit 6 containing valve 7. The conduit 6 is in fluid communication with a gas-chromatographic column 8 which in turn is in fluid communication with a conduit 10. The conduit 10 discharges to an ionizer 12 which in turn, discharges to a conduit 13. The conduit 13 is in fluid communication with a container 14 containing a bed 15 of mercuric oxide. The container 14 discharges to a conduit 16 which in turn is in fluid communication with an optical sensor 17. The optical sensor 17 optically senses the mercury vapour released from the bed 15 of mercuric oxide. The optical sensor 17 is connected to a chart recorder 18 which records observed values from the optical sensor 17.

In operation the valve 7 is opened permitting impure inert gas to flow from the container 4 through the conduit 6 and into the column 8. As is well known in the gas-chromatographic art, in the column 8 the impurities are separated such that they leave in sequence when the impure inert gas leaves the column 8 and enters the conduit 10. In the ionizer 12, the impurities are ionized such that they react with the mercuric oxide in the bed 15 releasing the mercury vapour. The amount of mercury vapour is directly proportional to the amount of the impurity. Since the column 8 has separated the impurities, the optical sensor 17 first senses mercury vapour from the first received impurity and then subsequently senses mercury vapour released from subsequent impurities. The chart recorder 18 produces a chart 18', practical examples of which are shown in this case in the form of FIGS. 3 and 4.

Referring now to FIG. 2 there is shown in cross-section a preferred embodiment of an ionizer 12 capable of internally generating an ionizing discharge which has surprisingly been found to allow the measurement of the presence of traces of non-reducing gases in impure inert gas. Although the mechanism by which this takes place is not completely clear it is believed that the discharge occuring within ionizer 12 provokes a type of cracking of the non-reducing gases such as $CO_2$ and $CH_4$ freeing respectively CO and $H_2$. These gases then react with the mercuric oxide present in the bed 15 releasing mercury vapour. The mercury vapour is then detected and measured by optical sensor 17.

Although the ionizing discharge acting on the impure inert gas can be obtained in various ways for example also by means of high frequency waves it has been found preferable to obtain this discharge by means of an ionizer 12 the preferred embodiment of which is shown in FIG. 2. The ionizer 12 comprises a body 20 with an inlet 21 and an outlet 22 for connection by conduit 10 to the gas-chromatographic separation column 8 and by conduit 16 to the optical sensor 17. Inlet 21 is connected by a passage 22' with cylindrical chamber 23 in which there is located an electrode 24 which defines, with the internal wall of said chamber 23 an annular space through which impure inert gas is obliged to flow. This gas then reaches outlet 22 through channel 25.

The electrode 24 is connected to an external source of high voltage by means of an insulating element 26 which is gastight. The high voltage which must be connected to the electrode 24 in order to obtain the required discharge depends upon the dimensions of the surrounding space that is to say of the ionizing chamber 23, and it also depends on the type of gas to be analyzed. An indicative range of values is approximately from 150 to 1000 volts. The polarity may be either positive or negative with respect to the outer wall connected to ground. The higher values are required for example with the gas nitrogen. The resistance of the electrode 24 should be sufficiently high to limit the value of current which is generated during the discharge. In the embodiment of FIG. 2 the discharge preferably takes place in a symmetrical manner about electrode 24 which is within the annular space between the electrode and the wall of chamber 23 and therefore acts on all the gas which flows through this area.

As used herein the term impure inert gas refers to a gas or vapour the major component of which does not react with mercuric oxide. Examples of impure inert gases include nitrogen, and the rare gases namely argon, neon, krypton, helium, xenon, and mixtures thereof.

EXAMPLE 1

The apparatus of FIG. 1 was operated using an impure inert gas 10 comprising helium containing the following impurities as manufactured by a speciality gas supplier: $CO_2$ (2.4 ppm); CO (1.7 ppm); $H_2$ (1.5 ppm); $CH_4$ (1.3 ppm). While ionizer 12 was not acting and electrode 24 had no voltage applied. In this case the apparatus behaves as described in the U.S. Pat. No. '867 in which mercuric oxide in the bed 15 is active only towards reducing gases. Chart recorder 18 therefore only indicates the peaks relative to CO and $H_2$ as shown in FIG. 3.

EXAMPLE 2

The same gas as used for Example 1 was made to flow through the apparatus 2 of the present invention. This time ionizer 12 had electrode 24 connected to a high voltage source of −430 volts, with a resistance of one megaohm. The wall of chamber 23 was connected to ground. A symmetrical cylindrical discharge takes place in all the gas as it flows on the ionizing electrode 24 which ionization is probably in the form of a plasma. The graph obtained on chart recorder 18 now shows four peaks that is to say again those relative to CO and $H_2$, in the same position, and furthermore distinctly separated there are another two peaks one for $CO_2$ and one for $CH_4$ as shown in FIG. 4.

In FIGS. 3 and 4 concentration is shown on the y-axis. The units on the y-axis are arbitrary. The scale of the y-axis of FIG. 3 and the scale of the y-axis of FIG. 4 are not uniform. In FIGS. 3 and 4 the x-axis is time which increases from right to left. This is because these figures represent the chart 18' wherein any given point moves from left to right.

Although the invention has been described in considerable detail with reference to certain preferred embodiments designed to teach those skilled in the art how best to practice the invention, it will be realized that other modifications may be employed without departing from the spirit and scope of the appended claims.

What is claimed is:

1. In a method for the detection of traces of impurity gases in an impure inert gas comprising the stages of passing the impure inert gas through a gas-chromatographic separation column and over a bed of mercuric oxide for the optical measurement of the quantity of mercury released from said bed; the improvement comprising a step between the chromatographic separation and the passage over the bed of mercuric oxide, in which the impure inert gas is subjected to an ionizing discharge which produces cracked impurity gases thereby producing reducing gases capable of reacting with the mercuric oxide thereby releasing mercury vapor in an amount directly proportional to the cracked impurity gases present in the inert impure gas.

2. A method of claim 1 characterized by the fact that said ionizing discharge is obtained by passing the impure inert gas to be analyzed around an electrode maintained at a voltage, positive or negative with respect to ground which has a value of from 150 to 1000 volts.

3. In an apparatus for the detection of the presence of trace gases as impurities in an impure inert gas comprising a gas-chromatographic separation column, and a mercury vapor detection device having a bed of mercuric oxide connected to a detector of a mercury vapour, the improvement comprising, an ionizer in series between said column and said detector with a passage through which the impure inert gas to be analyzed is obliged to flow, within which there is an electrode capable of generating an ionizing discharge which produces cracked impurity gases thereby producing reducing gases capable of reacting with the mercuric oxide thereby releasing mercury vapor in an amount directly proportional to the cracked impurity gases present in the inert impure gas.

4. An apparatus of claim 3, characterized by the fact that said passage is within a body which has mounted, with a suitable insulating and gastight insulator, said electrode; said passage comprising a cylindrical chamber within which there is coaxially placed said electrode.

5. An apparatus of claim 4, in which said electrode is connected by an insulator to an external source of voltage having a value from 150 to 1000 volts while the walls of said chamber are connected to a ground.

6. A method of determining the amount of methane present in an impure inert gas contaminated with trace amounts of methane said method comprising the steps of:

I. passing the impure inert gas through a gas chromatographic separation column; and then II. subjecting the impure gas to an ionizing discharge thereby cracking the methane into hydrogen and other components thereby producing ionized gas; and then III. contacting the ionized gas with mercuric oxide thereby producing mercury vapour in an amount directly proportional to the amount of methane present in the impure inert gas; and then IV. determining the amount of methane present by determining the amount of mercury vapour produced.

7. A method of determining the amount of carbon dioxide present in an impure inert gas contaminated with trace amounts of carbon dioxide said method comprising the steps of:

I. passing the impure inert gas through a gas-chromatographic separation column; and then II. subjecting the impure gas to an ionizing discharge thereby cracking the carbon dioxide into carbon monoxide and other components thereby producing ionized gas; and then III. contacting the ionized gas with mercuric oxide thereby producing memory vapour in an amount directly proportional to the amount of carbon dioxide present in the impure inert gas; and then IV. determining the amount of carbon dioxide present by determining the amount of mercury vapour produced.

8. A method of determining the amount of carbon dioxide and methane present in an impure inert gas contaminated with trace amounts of carbon dioxide and methane; said method comprising the steps of:

I. passing a given quantity of the impure inert gas as a stream through a gas-chromatographic separation column thereby concentrating the carbon dioxide at a specific place in the stream and also concentrating the methane at a different specific place in the stream; and then II. subjecting the stream of the impure gas to an ionizing discharge thereby cracking the carbon dioxide into carbon monoxide and other components and cracking the methane into hydrogen and other components thereby producing a gas to be tested; and then III. contacting the gas to be tested with mercuric oxide whereupon the carbon monoxide from the cracked carbon dioxide reduces some of the mercuric oxide thereby producing mercury vapour in an amount directly proportional to the amount of carbon dioxide present in the impure inert gas; whereupon the hydrogen from the cracked methane reduces some of the mercuric oxide thereby producing mercury vapour in an amount directly proportional to the amount of methane present in the impure inert gas; and then IV. determining the amount of carbon dioxide and methane present by determining the amount of mercury vapour produced at specific points in the gas stream.

* * * * *

UNITED STATES PATENT AND TRADEMARK OFFICE
CERTIFICATE OF CORRECTION

PATENT NO. : 4,889,814
DATED : December 26, 1989
INVENTOR(S) : Marco Succi

It is certified that error appears in the above-identified patent and that said Letters Patent is hereby corrected as shown below:

In Claim 7, in Column 5 at line 17,
    for --memory-- read "mercury".

Signed and Sealed this

Third Day of September, 1991

*Attest:*

HARRY F. MANBECK, JR.

*Attesting Officer*      *Commissioner of Patents and Trademarks*